US009271846B2

(12) United States Patent
Lim et al.

(10) Patent No.: US 9,271,846 B2
(45) Date of Patent: Mar. 1, 2016

(54) EXPANDING INTERBODY IMPLANT AND ARTICULATING INSERTER AND METHOD

(71) Applicant: WARSAW ORTHOPEDIC, INC., Warsaw, IN (US)

(72) Inventors: Roy K. Lim, Germantown, TN (US); Kevin T. Foley, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/622,305

(22) Filed: Feb. 13, 2015

(65) Prior Publication Data
US 2015/0150691 A1 Jun. 4, 2015

Related U.S. Application Data

(63) Continuation of application No. 14/034,811, filed on Sep. 24, 2013, now Pat. No. 8,986,389, which is a continuation of application No. 12/940,415, filed on Nov. 5, 2010, now Pat. No. 8,579,981, which is a continuation of application No. 10/763,115, filed on Jan. 22, 2004, now Pat. No. 7,828,849.

(60) Provisional application No. 60/444,561, filed on Feb. 3, 2003.

(51) Int. Cl.
*A61F 2/44* (2006.01)
*A61B 17/02* (2006.01)
(Continued)

(52) U.S. Cl.
CPC .............. *A61F 2/4465* (2013.01); *A61B 17/025* (2013.01); *A61F 2/442* (2013.01); *A61F 2/4611* (2013.01); *A61B 17/00234* (2013.01); *A61B 2017/0256* (2013.01); *A61F 2/30767* (2013.01); *A61F 2002/2817* (2013.01); *A61F 2002/2835* (2013.01); *A61F 2002/3055* (2013.01); *A61F 2002/30133* (2013.01); *A61F 2002/30428* (2013.01); *A61F 2002/30471* (2013.01); *A61F 2002/30481* (2013.01); *A61F 2002/30492* (2013.01); *A61F 2002/30505* (2013.01); *A61F 2002/30538* (2013.01); *A61F 2002/30556* (2013.01); *A61F 2002/30561* (2013.01); *A61F 2002/30579* (2013.01);
(Continued)

(58) Field of Classification Search
CPC .......................... A61F 2/4465; A61F 2/30579
USPC ............................................. 623/17.11–17.16
See application file for complete search history.

(56) References Cited

U.S. PATENT DOCUMENTS 4,743,256 A 5/1988 Brantigan
4,834,757 A 5/1989 Brantigan
(Continued)

FOREIGN PATENT DOCUMENTS

FR 2824261 5/2004
WO WO 9700054 3/1997
(Continued)

*Primary Examiner* — Pedro Philogene
*Assistant Examiner* — David C Comstock

(57) ABSTRACT

A device to space vertebral members with first and second members that may have at least one ramped section. The first and second members may be positioned in a vertically overlapping arrangement with interior sides of the members facing together. The device may be positionable between a first orientation with the ramped section of the first member positioned away from the ramped section of the second member, and a second orientation with the ramped section of the first member positioned against the ramped section of the second member. The device may include a greater height measured between the exterior sides in the second orientation than in the first orientation.

20 Claims, 14 Drawing Sheets

(51) Int. Cl.
*A61F 2/46* (2006.01)
*A61B 17/00* (2006.01)
*A61F 2/30* (2006.01)
*A61F 2/28* (2006.01)

(52) U.S. Cl.
CPC .............. *A61F 2002/30601* (2013.01); *A61F 2002/30772* (2013.01); *A61F 2002/4623* (2013.01); *A61F 2002/4627* (2013.01); *A61F 2002/4628* (2013.01); *A61F 2002/4635* (2013.01); *A61F 2220/0025* (2013.01); *A61F 2220/0091* (2013.01); *A61F 2230/0015* (2013.01); *A61F 2250/0006* (2013.01); *A61F 2250/0009* (2013.01)

(56) References Cited

U.S. PATENT DOCUMENTS

| | | |
|---|---|---|
| 4,863,476 A | 9/1989 | Shepperd |
| 4,878,915 A | 11/1989 | Brantigan |
| 5,171,278 A | 12/1992 | Pisharodi |
| 5,192,327 A | 3/1993 | Brantigan |
| 5,425,772 A | 6/1995 | Brantigan |
| 5,443,514 A | 8/1995 | Steffee |
| 5,484,437 A | 1/1996 | Michelson |
| 5,505,732 A | 4/1996 | Michelson |
| 5,522,899 A | 6/1996 | Michelson |
| 5,554,191 A | 9/1996 | Lahille et al. |
| D377,096 S | 12/1996 | Michelson |
| 5,609,635 A | 3/1997 | Michelson |
| 5,653,763 A | 8/1997 | Errico et al. |
| 5,658,335 A | 8/1997 | Allen |
| 5,665,122 A | 9/1997 | Kambie |
| 5,716,415 A | 2/1998 | Steffee |
| 5,755,732 A | 5/1998 | Green et al. |
| 5,766,252 A | 6/1998 | Henry |
| 5,776,199 A | 7/1998 | Michelson |
| 5,782,830 A | 7/1998 | Farris |
| 5,865,848 A | 2/1999 | Baker |
| 5,888,224 A | 3/1999 | Beckers et al. |
| 5,888,227 A | 3/1999 | Cottle |
| 5,893,889 A | 4/1999 | Harrington |
| 5,895,426 A | 4/1999 | Scarborough et al. |
| 5,980,522 A | 11/1999 | Koros |
| 5,984,922 A | 11/1999 | McKay |
| 6,045,579 A | 4/2000 | Hochshuler |
| 6,080,158 A | 6/2000 | Lin |
| 6,080,193 A | 6/2000 | Hochshuler et al. |
| 6,090,143 A | 7/2000 | Meriwether et al. |
| 6,102,950 A | 8/2000 | Vaccaro |
| 6,113,638 A | 9/2000 | Williams et al. |
| 6,117,174 A | 9/2000 | Nolan |
| 6,159,245 A | 12/2000 | Meriwether et al. |
| 6,176,881 B1 | 1/2001 | Schar et al. |
| 6,176,882 B1 | 1/2001 | Biedermann |
| 6,183,517 B1 | 2/2001 | Suddaby |
| 6,190,414 B1 | 2/2001 | Young et al. |
| 6,217,579 B1 | 4/2001 | Koros |
| 6,245,108 B1 | 6/2001 | Biscup |
| 6,319,257 B1 | 11/2001 | Carignan et al. |
| 6,368,351 B1 | 4/2002 | Glenn et al. |
| 6,371,989 B1 | 4/2002 | Chauvin et al. |
| 6,419,705 B1 | 7/2002 | Erickson |
| 6,419,706 B1 | 7/2002 | Graf |
| 6,432,108 B1 | 8/2002 | Burgess et al. |
| 6,436,140 B1 | 8/2002 | Liu et al. |
| 6,436,142 B1 | 8/2002 | Paes et al. |
| 6,443,989 B1 | 9/2002 | Jackson |
| 6,454,806 B1 | 9/2002 | Cohen et al. |
| 6,454,807 B1 | 9/2002 | Jackson |
| 6,468,276 B1 | 10/2002 | McKay |
| 6,517,051 B1 | 2/2003 | Cavanaugh |
| 6,562,074 B2 | 5/2003 | Gerbec et al. |
| 6,576,016 B1 | 6/2003 | Hochshuler et al. |
| 6,641,614 B1 | 11/2003 | Wagner et al. |
| 6,648,917 B2 | 11/2003 | Gerbec et al. |
| 6,676,703 B2 | 1/2004 | Biscup |
| 6,685,742 B1 | 2/2004 | Jackson |
| 6,706,070 B1 | 3/2004 | Wagner et al. |
| 6,767,366 B2 | 7/2004 | Lee et al. |
| 6,830,589 B2 | 12/2004 | Erickson |
| 6,835,206 B2 | 12/2004 | Jackson |
| 6,852,129 B2 | 2/2005 | Gerbec et al. |
| 6,863,673 B2 | 3/2005 | Gerbec et al. |
| 6,893,464 B2 | 5/2005 | Kiester |
| 7,204,853 B2 | 4/2007 | Gordon et al. |
| 7,211,112 B2 | 5/2007 | Baynham et |
| 7,217,293 B2 | 5/2007 | Branch, Jr. |
| 7,316,714 B2 | 1/2008 | Gordon et al. |
| 7,569,074 B2 | 8/2009 | Eisermann et al. |
| 7,594,932 B2 | 9/2009 | Aferzon et al. |
| 7,744,649 B2 | 6/2010 | Moore |
| 7,749,270 B2 | 7/2010 | Peterman |
| 7,753,958 B2 | 7/2010 | Gordon |
| 7,850,733 B2 | 12/2010 | Baynham et al. |
| 7,875,078 B2 | 1/2011 | Wysocki et al. |
| 7,909,869 B2 | 3/2011 | Gordon et al. |
| 8,062,375 B2 | 11/2011 | Glerum et al. |
| 8,105,382 B2 | 1/2012 | Olmos et al. |
| 8,123,810 B2 | 2/2012 | Gordan et al. |
| 8,133,232 B2 | 3/2012 | Levy et al. |
| 2001/0032020 A1 | 10/2001 | Besselink |
| 2002/0045943 A1 | 4/2002 | Uk |
| 2002/0045945 A1 | 4/2002 | Liu et al. |
| 2002/0068976 A1 | 6/2002 | Jackson |
| 2002/0068977 A1 | 6/2002 | Jackson |
| 2002/0128713 A1 | 9/2002 | Ferree |
| 2002/0128716 A1 | 9/2002 | Cohen et al. |
| 2002/0138146 A1 | 9/2002 | Jackson |
| 2002/0143401 A1 | 10/2002 | Michelson |
| 2002/0177897 A1 | 11/2002 | Michelson |
| 2003/0130739 A1 | 7/2003 | Gerbec et al. |
| 2003/0139812 A1 | 7/2003 | Garcia et al. |
| 2003/0149484 A1 | 8/2003 | Michelson |
| 2004/0059421 A1 | 3/2004 | Glenn et al. |
| 2004/0087947 A1 | 5/2004 | Lim et al. |
| 2004/0102847 A1 | 5/2004 | Sato et al. |
| 2004/0127993 A1 | 7/2004 | Kast et al. |
| 2004/0127994 A1 | 7/2004 | Kast et al. |
| 2005/0278026 A1 | 12/2005 | Gordon et al. |
| 2006/0247770 A1 | 11/2006 | Peterman |
| 2007/0270968 A1 | 11/2007 | Baynham et al. |
| 2008/0147193 A1 | 6/2008 | Matthis et al. |
| 2009/0222100 A1 | 9/2009 | Cipoletti et al. |
| 2010/0286779 A1 | 11/2010 | Thibodeau |
| 2011/0172774 A1 | 7/2011 | Varela |

FOREIGN PATENT DOCUMENTS

| | | |
|---|---|---|
| WO | WO 9848738 | 11/1998 |
| WO | WO 9932054 | 1/1999 |
| WO | WO 9942062 | 8/1999 |
| WO | WO 0074605 | 12/2000 |

EXPANDING INTERBODY IMPLANT AND ARTICULATING INSERTER AND METHOD

RELATED APPLICATIONS

This application is a continuation of U.S. patent application Ser. No. 14/034,811, filed on Sep. 24, 2013, which is a continuation of Ser. No. 12/940,415, filed on Nov. 5, 2010, which is a continuation of U.S. patent application Ser. No. 10/763,115, filed on Jan. 22, 2004, which claims priority to U.S. provisional application Ser. No. 60/444,561, filed on Feb. 3, 2003. These applications are expressly incorporated in their entirety herein by reference.

BACKGROUND

Various devices are used for controlling the spacing between vertebral members. These devices may be used on a temporary basis, such as during surgery when it is necessary to access the specific surfaces of the vertebral member. One example includes preparing the endplates of a vertebral member. The devices may also remain permanently within the patient to space the vertebral members.

It is often difficult to position the device between the vertebral members in a minimally invasive manner. A device that is small may be inserted into the patient and between the vertebral members in a minimally invasive manner. However, the small size may not be adequate to effectively space the vertebral members. A larger device may be effective to space the vertebral members, but cannot be inserted into the patient and between the vertebral members in a minimally invasive manner.

SUMMARY

The present application is directed to devices to space vertebral members. One device may include first and second elongated, non-annular members each with opposing first and second ends, an exterior side, and an opposing interior side with at least one ramped section. The first member may further include a sidewall on the interior side positioned closer to a perimeter of the first member than the ramped section. The sidewall may have a height greater than the ramped section to extend outward from the interior side beyond the ramped section. The first and second members may be positioned in a vertically overlapping arrangement with the interior sides facing together and the sidewall in a horizontally overlapping arrangement with second member. The device may be positionable between a first orientation with the ramped section of the first member positioned away from the ramped section of the second member, and a second orientation with the ramped section of the first member positioned against the ramped section of the second member. The device may include a greater height measured between the exterior sides in the second orientation than in the first orientation.

A device may also include a base member, a first ramped member with a first side that abuts against the base member and an opposing second side that includes a first ramped section, and a second ramped member with a first side having a second ramped section that faces towards the first ramped member and an opposing second side that may face away from the base member. The base member and first and second ramped members may be in a vertically overlapping arrangement. The base member may be in a horizontally overlapping arrangement with the first ramped member. The first ramped member may be configured to move laterally relative to the base member between a first orientation with the first and second ramped sections positioned apart and a second orientation with the first and second ramped sections positioned in contact. The second ramped member may be operatively connected to the base member to move vertically away from the base member while being constrained from moving horizontally when the first ramped member moves from the first orientation to the second orientation.

A device may also include a base member, a first ramped member including a first side that abuts against the base member and an opposing second side that includes first and second ramped sections, and a second ramped member including a first side with third and fourth ramped sections that are aligned towards the first ramped member. The second ramped member may further include an opposing second side that faces away from the base member. The device may have a longitudinal axis that extends through opposing first and second ends of each of the base member and first and second ramped members. The longitudinal axis may further extend through each of the first, second, third, and fourth ramped sections. The first ramped member may be configured to move along the longitudinal axis relative to the base member and the second ramped member between a first orientation with the first and third ramped sections positioned apart, and the second and fourth ramped sections positioned apart, and a second orientation with the first and third ramped sections abutting together and the second and fourth ramped sections abutting together. The second ramped member may be operatively connected to the base member to move vertically away from the base member and may be constrained from moving along the longitudinal axis when the first ramped member moves from the first orientation to the second orientation.

DETAILED DESCRIPTION

Figure 1:
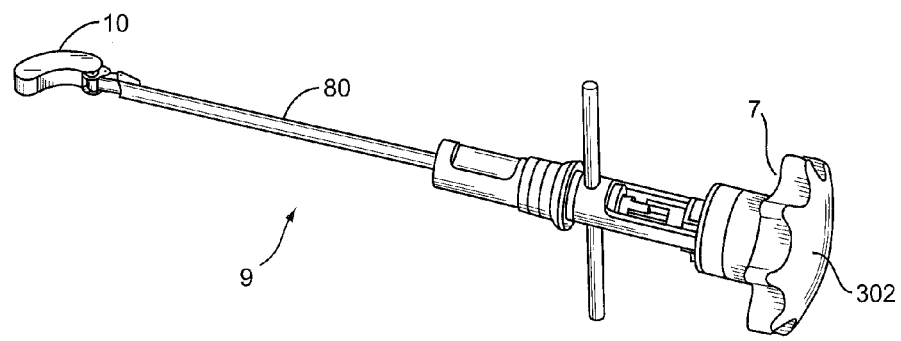
FIG. 1 is a perspective view of one embodiment of the present invention.

The present invention is directed to a device for positioning between adjacent vertebral members. FIG. 1 illustrates one embodiment, generally indicated as 9, which includes a spacer 10, delivery device 80, and a deployer 7. Spacer 10 is positioned between adjacent vertebral members and is selectively adjustable between a closed orientation, open orientation, and gradations therebetween. Delivery device 80 functions to position the spacer within the patient. Deployer 7 moves the spacer to the selected expanded orientations.

Figure 2:
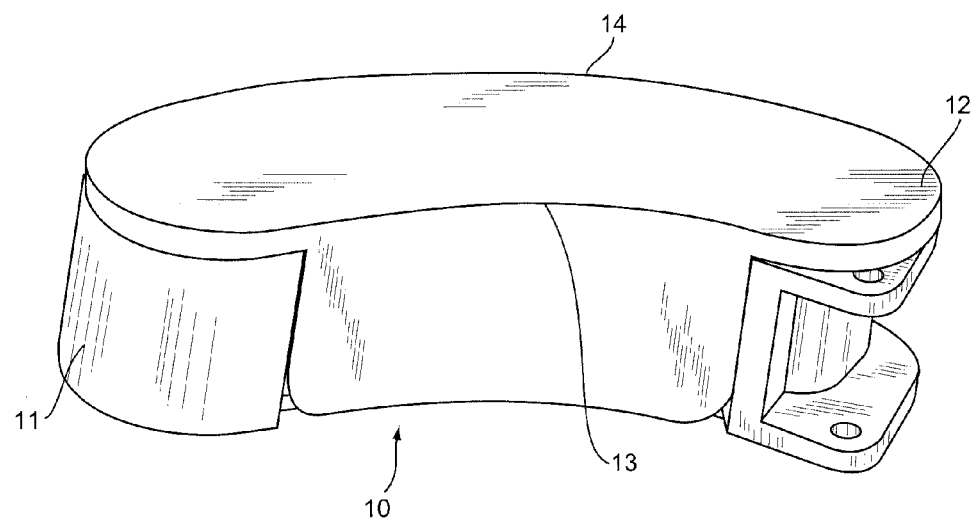
FIG. 2 is a perspective view of the spacer in a closed orientation according to one embodiment of the present invention.
Figure 3:
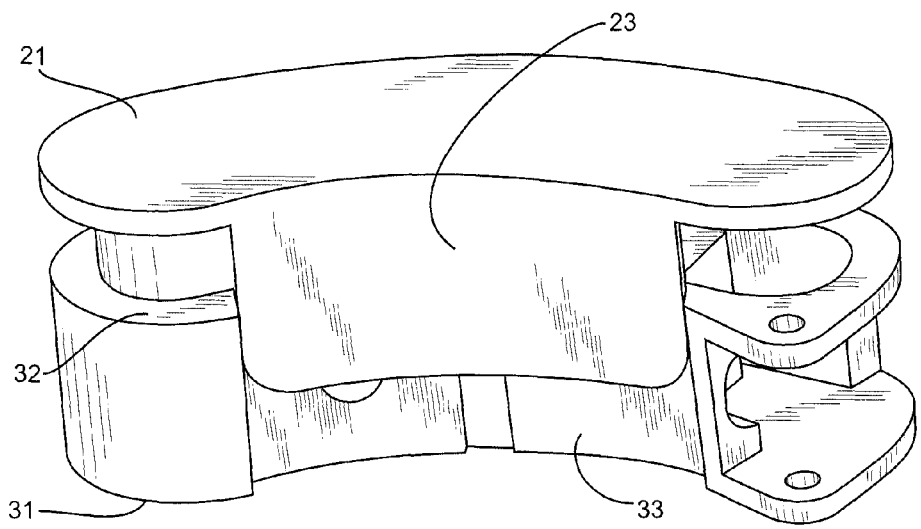
FIG. 3 is a perspective view of the spacer in an open orientation according to one embodiment of the present invention.

Spacer 10 has a variety of shapes and sizes depending upon the application, such as an elongated, curved shape. The spacer 10 is adjustable between a first position as illustrated in FIG. 2 having a reduced size to be minimally invasive when inserted into the patient between the vertebral members. FIG. 3 illustrates a second position with the spacer 10 expanded to contact the vertebral members. The spacer 10 may be expandable to a variety of different heights depending upon the desired application.

FIGS. 2 and 3 illustrate one embodiment of the spacer 10 having a rounded kidney shape with a first distal end 11 and second proximal end 12 each having a rounded shape. First and second sides 13, 14 are curved. The spacer 10 may have a substantially constant width, with one specific embodiment having a width of about 33 mm. The height of the spacer 10 may vary depending upon the amount of deployment and is dictated by the angle of the ramped surfaces as will be described in detail below. In one specific embodiment, spacer 10 has a height ranging from about 9 mm to about 13 mm. In one embodiment, the spacer 10 is angled in one or more of the closed, open, or deploying orientations to conform to the dimensions of the vertebral member.

Figure 4:
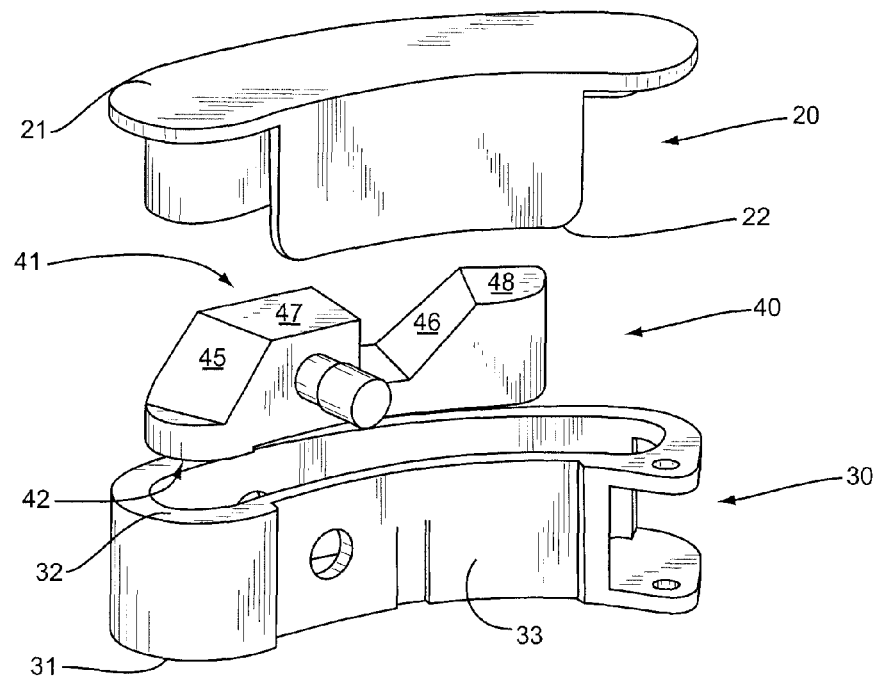
FIG. 4 is an exploded perspective view of the spacer according to one embodiment of the present invention.

FIG. 4 illustrates one embodiment of the spacer 10 including a first member 20, a second member 30, and a third member 40. First member 20 includes contact surface 21 and second member 30 includes contact surface 31 each for contacting a vertebral member. Contact surfaces 21, 31 may be substantially smooth, or may have stabilization features such as ridges or knurls to contact the vertebral members.

First and second members 20, 30 have complementary shapes to mate together in the closed orientation. Outward edges 22, 32 of the members 20, 30 are adjacently positioned in the closed orientation to reduce the overall size of the spacer 10. Outward edge 32 may contact or be spaced apart from the inner edge of the contact surface 21 when the spacer 10 is in the closed orientation. Sidewalls 23, 33 extend from the contact surfaces and may have a variety of different shapes and sizes to define the overall shape of the spacer 10.

Figure 5:
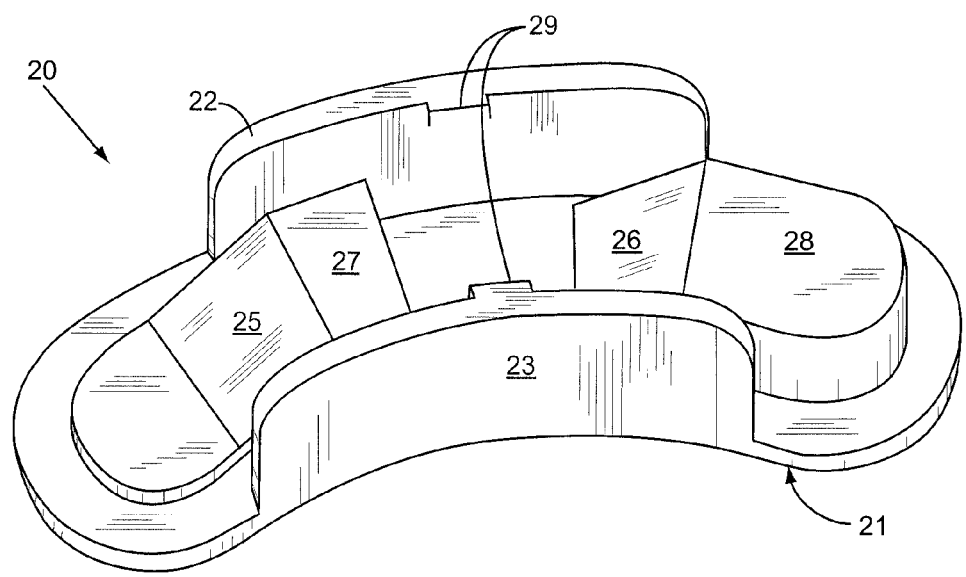
FIG. 5 is a perspective view of the first member according to one embodiment of the present invention.

FIG. 5 illustrates one embodiment of the underside of the first member 20. Sidewalls 23 extend outward to mate with the second member 30. A tab 29 may extend outward from one of the sidewalls 23 to mate with a groove in the second member sidewall 33 to further stabilize during deployment and when the spacer 10 is in the open orientations. Tabs 29 contact an upper edge of the groove (see FIG. 18) to prevent the first member 20 from separating from the second member 30 during deployment of the spacer 10.

First member 20 includes a first angled section 25 and a support section 27, and a second angled section 26 and support section 28. Angled sections 25, 26 may have a variety of lengths, and may be positioned at a variety of angles relative to the contact surface 21. The angled sections 26, 25 may be at the same angle, or may have different angles. In one embodiment, the range of angles between the sections 25, 26 and contact surface 21 is between about 20° to about 40°. Support sections 27, 28 are positioned adjacent to the angled sections 25, 26 and are positioned at a different angle relative to the angled sections 25, 26. In one embodiment, support sections 27, 28 are substantially parallel with the contact surface 21.

Figure 7:
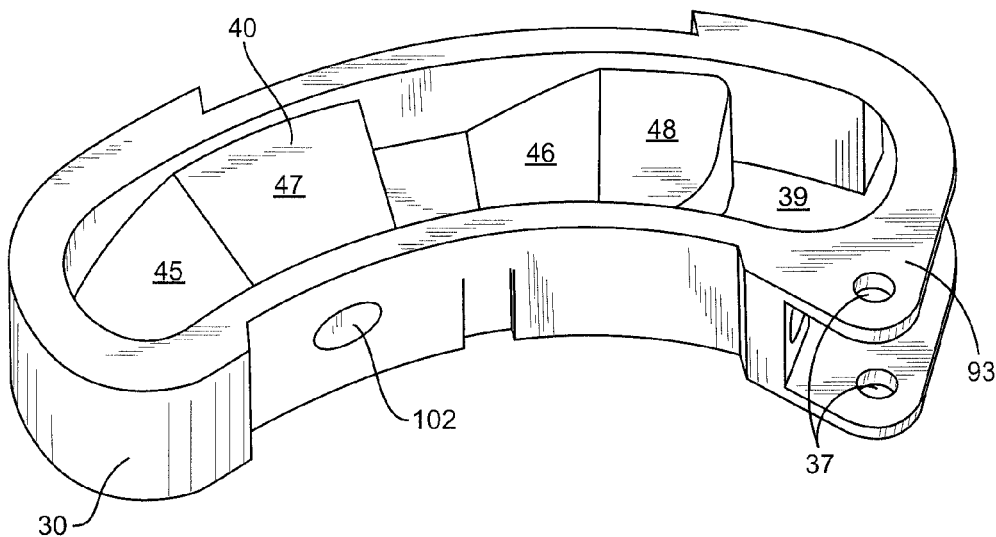
FIG. 7 is a perspective view of the third member in a second position within the second member according to one embodiment of the present invention.
Figure 8:
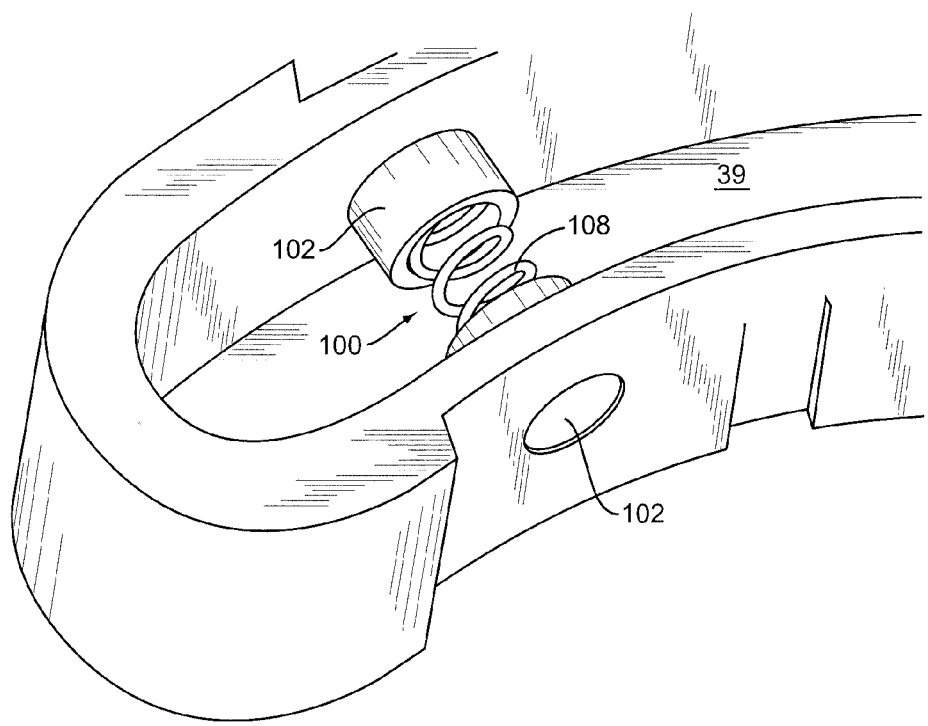
FIG. 8 is a partial cut-away perspective view of the locking mechanism according to one embodiment of the present invention.

The shape of the second member 30 complements the first member 20. Sidewalls 33 extend around a portion or the entirety of the second member 30 to align with the first member 20 and form an interior section to maintain the third member 40. An inner section 39 is formed within the sidewalls 33 opposite the contact surface 31. In one embodiment as illustrated in FIGS. 7 and 8, inner section 39 is substantially flat and smooth to facilitate the relative movement of the third member 40. A frame 93 may extend from the second member 30. Apertures 37 positioned on the frame 93 allow for attachment of the delivery device 80 as explained below.

Third member 40 is positioned between the first member 20 and second member 30. Third member 40 includes a first side 41 having angled sections 45, 46 that mate with the first member 20, and a second side 42 to contact the second member 30. One embodiment of the first side 41 is illustrated in FIG. 4 and includes a first angled section 45 and adjacent support section 47, and a second angled section 46 and support section 48. Angled sections 45, 46 may have a variety of lengths, and may be positioned at a variety of angles relative to the second side 42. In one embodiment, the range of angles between sections 45, 46 and second side 41 is between about 20° to about 40°. Support sections 47, 48 are positioned at a different angle relative to the angled sections 45, 46. In one embodiment, support sections 47, 48 are substantially parallel with the second side 42. In one embodiment, second side 42 is flat which complements a flat surface of the inner section 39.

Figure 6:
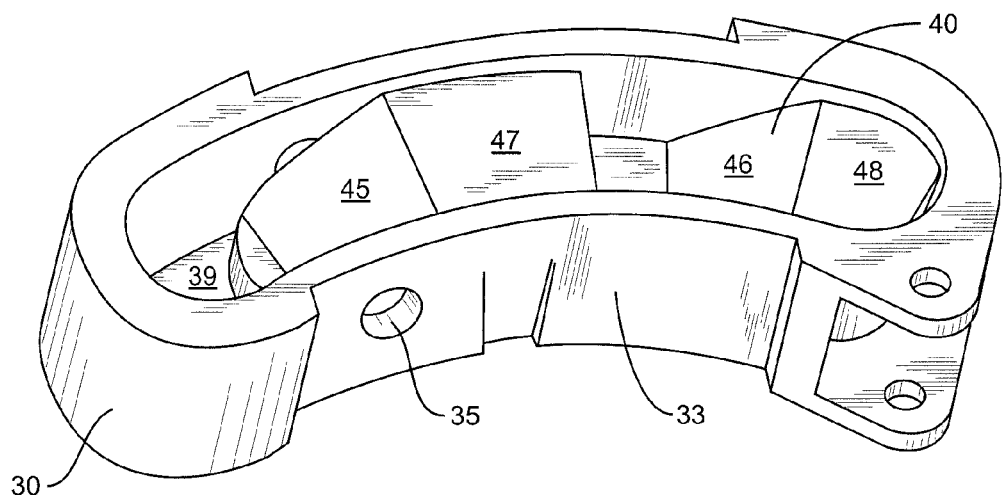
FIG. 6 is a perspective view of the third member in a first position within the second member according to one embodiment of the present invention.

Third member 40 may have a width and length less than or equal to the boundary formed by the sidewalls 33 of the second member 30. The smaller size provides for sliding movement of the third member 40 relative to the second member 30. The relative positioning of the second and third members 30, 40 is illustrated in FIGS. 6 and 7. FIG. 6 illustrates a first position with the third member 40 positioned against a proximal edge of the second member 30. FIG. 7 illustrates a second position with the third member 40 positioned against a distal edge of the second member 30.

Third member 40 moves relative to the first and second members 20, 30 to deploy the spacer 10 from the closed orientation to the open orientation. The spacer 10 may be positioned within the patient in the closed orientation that has a minimal size and shape to facilitate placement within the patient and between the vertebral members. The angled sections 25, 26, 45, 46 of the first and third members 20, 40 are disengaged in the closed orientation.

Deployment of the spacer 10 is caused by the third member 40 moving relative to the first member 20. Relative movement causes the angled sections 45, 46 of the third member 40 to contact the angled sections 25, 26 of the first member 20. This causes the first member 20 to move outward away from the centerline of the spacer 10. As the third member 40 is moved further, the angled sections continue to slide relative to one another and the first member 20 continues to move outward from the centerline increasing the overall height of the spacer 10.

Figure 9:
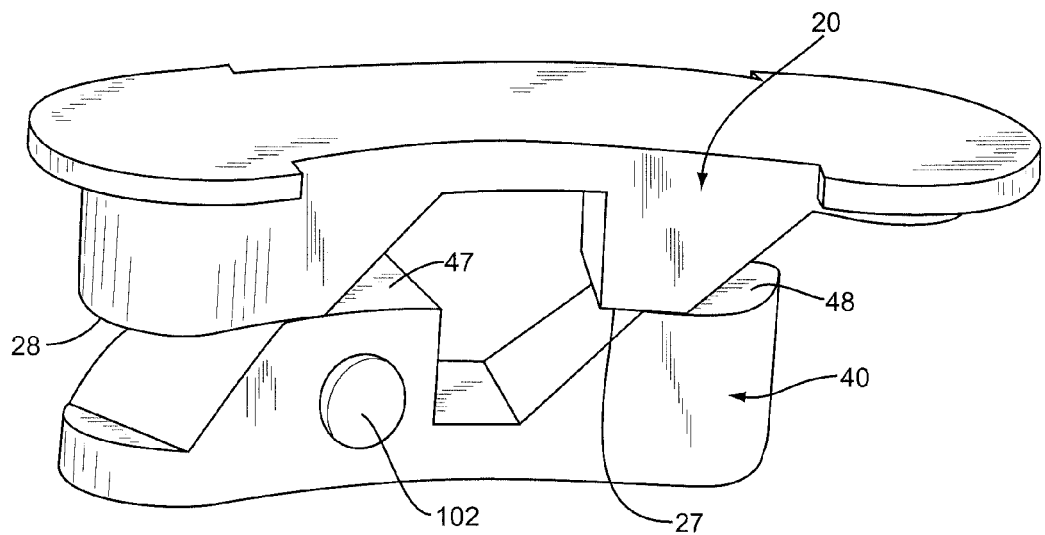
FIG. 9 is a perspective view of the first member in contact with the second member according to one embodiment of the present invention.
Figure 10:
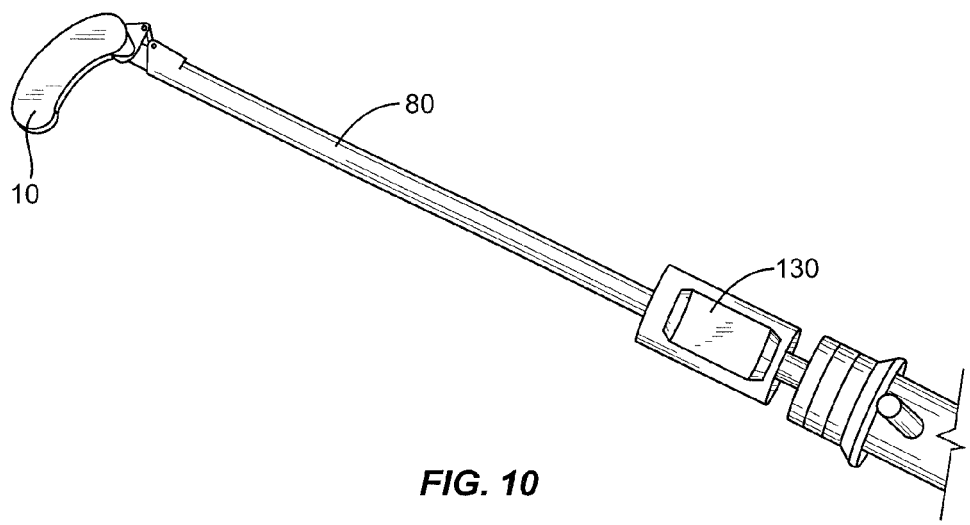
FIG. 10 is a partial perspective view of the spacer angled relative to the delivery device according to one embodiment of the present invention.

FIG. 9 illustrates one embodiment at the open position with full deployment. The sections 27, 28 on the first member 20 contact and rest on sections 47, 48 of the third member 40. In one embodiment, the sections 27, 28, 47, 48 are angled to a lesser amount than the angled sections 25, 26, 45, 46 to prevent the spacer 10 from moving towards the closed orientation. The angled sections 25, 26, 45, 46 may have the same angle.

The rounded shape of the spacer 10 results in the some or all of the angled sections of the first and third members 20, 40 having non-symmetrical shapes. In one embodiment illustrated in FIG. 5, angled sections 25, 26 have a shorter length on the first edge 13 than on the second edge 14. Likewise, the angled sections 25, 26 are not aligned because of the rounded shape of the second member 20. FIG. 6 illustrates that angled surfaces 45, 46 having a first inner edge shorter than the second outer edge, and the angled surfaces not being aligned.

The slope and sizes of the angled surfaces 25, 26, 45, 46 of the first and third members 20, 40 may vary to change the shape of the spacer 10 in the open orientation. The contact surfaces 21 and 31 may be oblique with the one end of the spacer 10 having a larger height than the other end, or may be substantially parallel in the open orientation and gradations of being open. The spacer 10 in the open orientation may be shaped to conform to the curvature of the spine.

In one embodiment, the spacer 10 includes two members each having angled sections and there is no third member. The angled sections of the first member contact the angled sections of the second member during the deployment. Each of the members may further include platform sections for contact in the open orientation.

The spacer 10 may expand in both a first and second direction. The third member 40 includes angled sections on the second side 42 that contact angled sections on the inner section 39 of the second member 30. In one embodiment, movement of the third member 40 results in both the first member 20 and second member 30 moving outward from a centerline of the spacer 10.

Another embodiment features one or more of the angled sections 25, 26, 45, 46 having a stepped configuration. The stepped configuration features an angled section having one or more steps positioned thereabout angled to a different degree. The steps are positioned along the angled sections 25, 26, 45, 46 for deploying the spacer 10 to differing extents. A variety of step surfaces may be positioned on the sections. In one embodiment, angled sections 25, 26, 45, 46 each include two steps with the spacer positionable between a closed orientation, first orientation on a first step, second orientation on a second step, and fully deployed orientation.

The first member 20 and the second member 30 may also each include a single angled section. Movement of the spacer 10 results in only the single angled surfaces contacting. The angled surfaces may be positioned at any point along the length of the spacer 10. In one embodiment, support surfaces are positioned adjacent to the angled surfaces.

A locking member 100 may lock the spacer 10 in a particular position. In one embodiment as illustrated in FIG. 8, locking member 100 includes a pair of caps 102 forced apart by a biasing member 108 (FIG. 8 features the third member 40 removed for clarity). Each cap 102 includes an extension 106 sized to fit within the apertures positioned within the first member 20 or second member 30. In one embodiment, a pair of apertures 35 are positioned on the third member 30 for receiving the locking member 100. As the third member 40 moves relative to the second member 20, the locking member 100 extends into one or more of the apertures 35. In one embodiment, apertures are positioned for receiving the caps 102 when the spacer 100 is at the open orientation and the support sections are in contact. In another embodiment, apertures 35 are positioned for receiving the caps 102 while the angled surfaces are in contact. The locking member 100 prevents the third member 40 from sliding outward and inadvertently reducing the spacer size. In a spacer 10 having a stepped configuration on the angled sections, aperture pairs may be positioned to lock the spacer at each gradation. In one embodiment, locking mechanism 100 includes a single cap 102 that is fit into a single aperture. A spacer is disclosed in previously filed U.S. patent application Ser. No. 10/229,560 entitled Minimally Invasive Expanding Spacer and Method, filed Aug. 28, 2002 and assigned to the same entity as the present application and herein incorporated by reference in its entirety.

Figure 12:
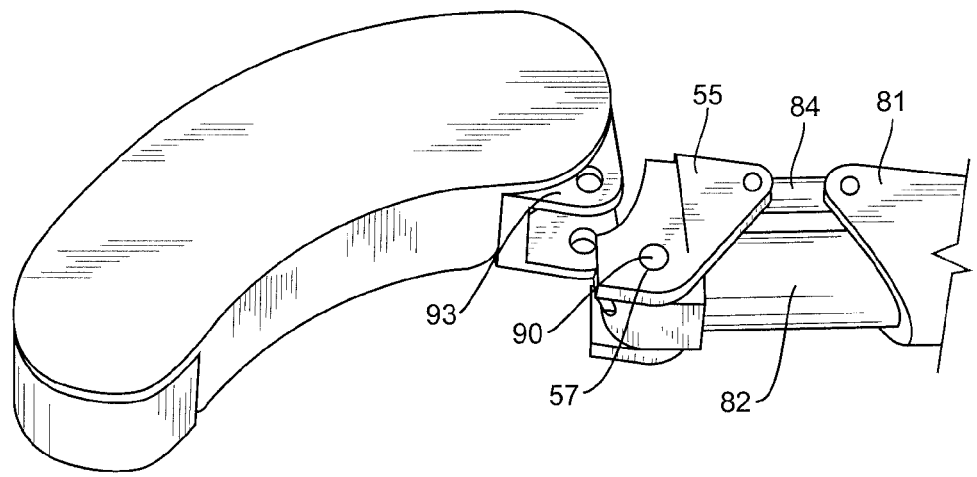
FIG. 12 is a partial perspective view of the spacer disengaged from the delivery device according to one embodiment of the present invention.
Figure 13:
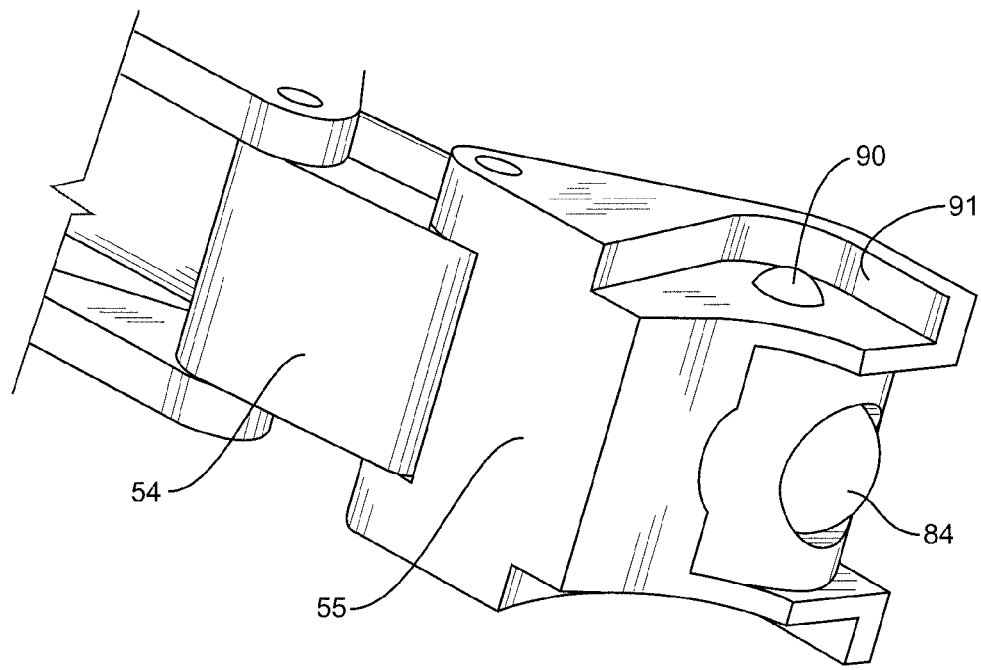
FIG. 13 is a partial perspective view of the holder and pivots in a first orientation according to one embodiment of the present invention.
Figure 14:
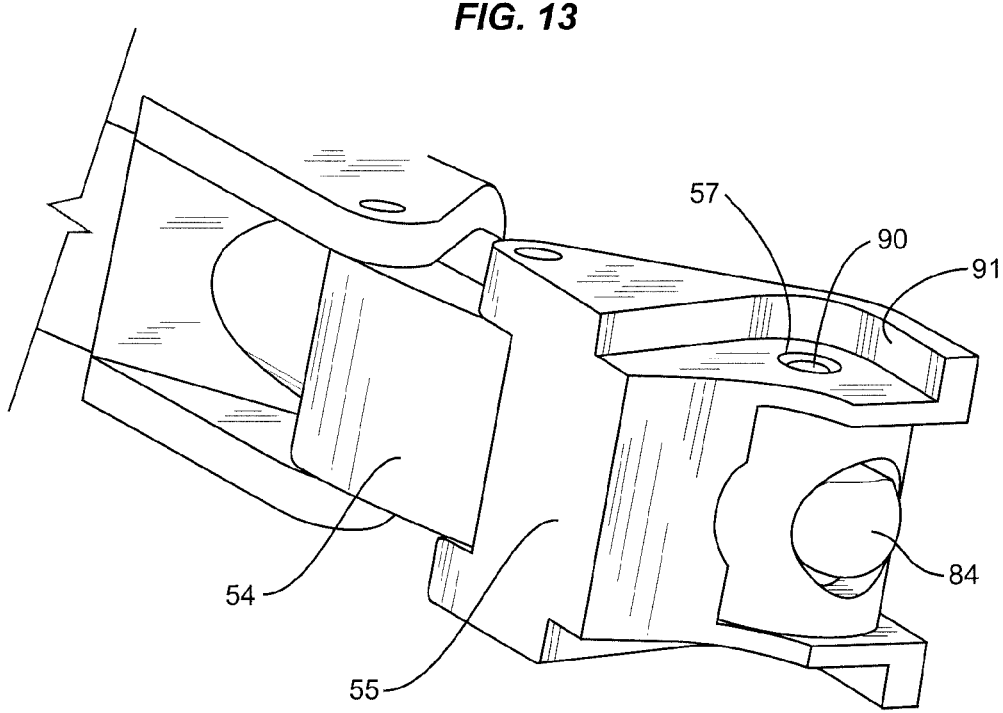
FIG. 14 is a partial perspective view of the holder and pivots in a second orientation according to one embodiment of the present invention.

The delivery device 80 functions to position the spacer 10 within the patient. Delivery device 80 has an elongated shape for the physician to position the spacer 10 within the patient between vertebral members. In one embodiment as illustrated in FIG. 12, delivery device 80 has an elongated shape sized with a distal end attached to the spacer 10 and a proximal end positioned exterior to the patient. Delivery device 80 may have a variety of cross-sectional shapes and sizes depending upon the application. Delivery device 80 may be constructed of a single elongated member, or may be constructed of different sections.

Figure 11:
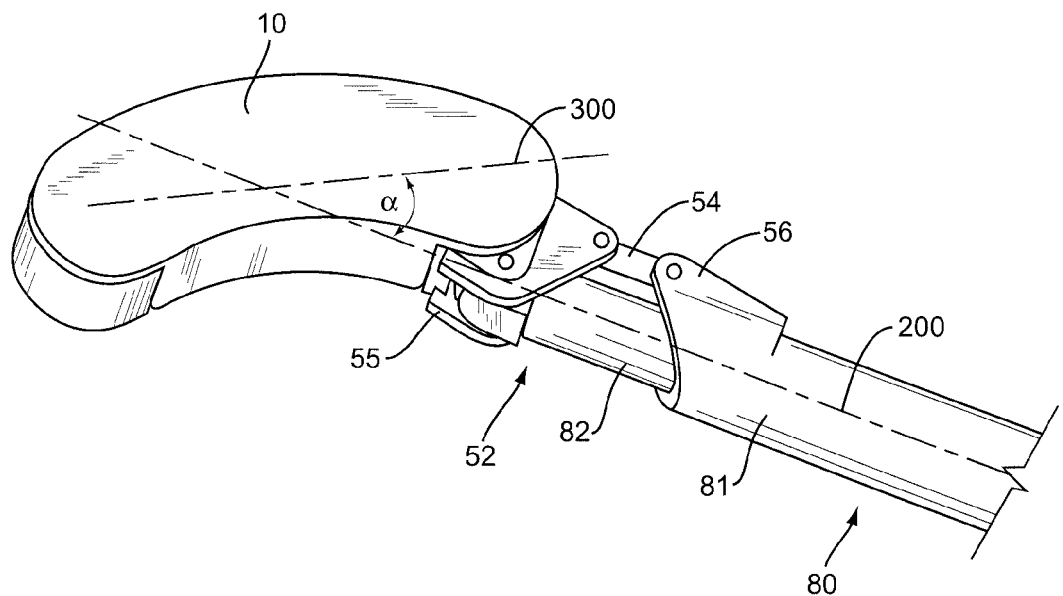
FIG. 11 is a partial perspective view of another embodiment of the spacer angled relative to the delivery device according to one embodiment of the present invention.

Delivery device 80 may be mounted to the spacer in a pivoting manner. FIG. 11 illustrates one embodiment of the delivery device 80 comprising a first shaft 81 and a second shaft 82. A holder 55 is positioned at the distal end of the shaft 82. Holder 55 includes apertures 57 through which live pivots 90 extend. In one embodiment, an angled edge 91 conforms with the spacer frame 93. A link 54 is pivotally mounted between holder 55 and the first shaft 81. The first shaft 81 is selectively positionable to pivot the holder 55 about the live pivots 90 and thus pivot the spacer 10 relative to the delivery device 80. A bracket 56 may be formed at the end of the first shaft 81 for attachment to the link 54.

In one embodiment, spacer 10 and delivery device 80 are positioned in a first orientation as illustrated in FIG. 11. A longitudinal axis 300 of the spacer 10 forms an acute angle α with a longitudinal axis 200 of the delivery device 80. This orientation provides for the footprint of the spacer 10 to be reduced during the insertion procedure such that the spacer 10 is positioned within the patient in a minimally invasive manner. In one embodiment, the longitudinal axis 300 is substantially aligned with the longitudinal axis 200 (i.e., angle α is less than about 10 degrees).

Figure 15:
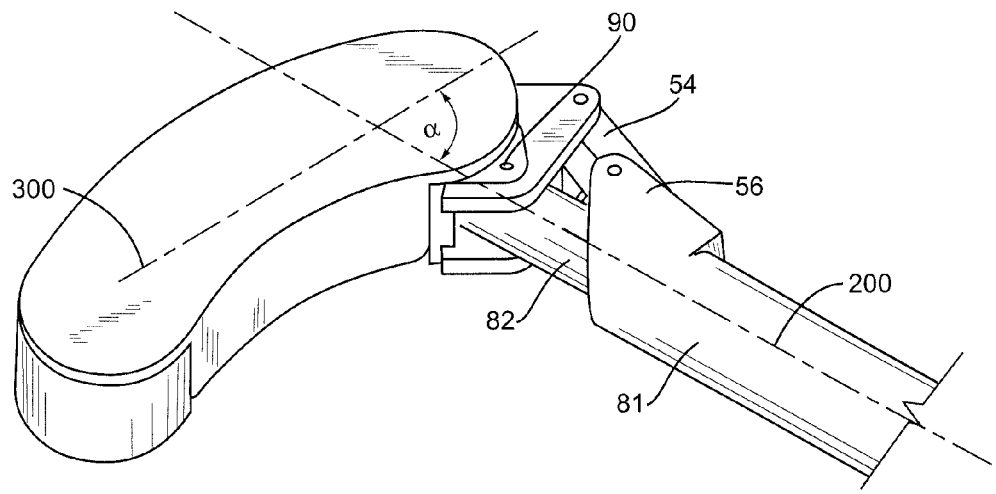
FIG. 15 is a partial perspective view of another embodiment of the spacer angled relative to the delivery device according to one embodiment of the present invention.

Once positioned between the vertebral members, spacer 10 is pivoted relative to the delivery device 80 as illustrated in FIG. 15. The spacer 10 is pivoted relative to the delivery device 80 such that angle α is increased from the first orientation. In one embodiment, angle α is increased to between about 75 and 110 degrees. In one embodiment, articulation is caused by moving the first shaft 81 relative to the second shaft 82. The holder 55 is connected to the second shaft 82 and relative movement of the first shaft 81 causes the holder 55 to pivot about pivots 90. The amount of relative movement of the shafts 81, 82 translates to the amount of articulation or angle of the spacer 10 relative to the delivery device 80.

Figure 16:
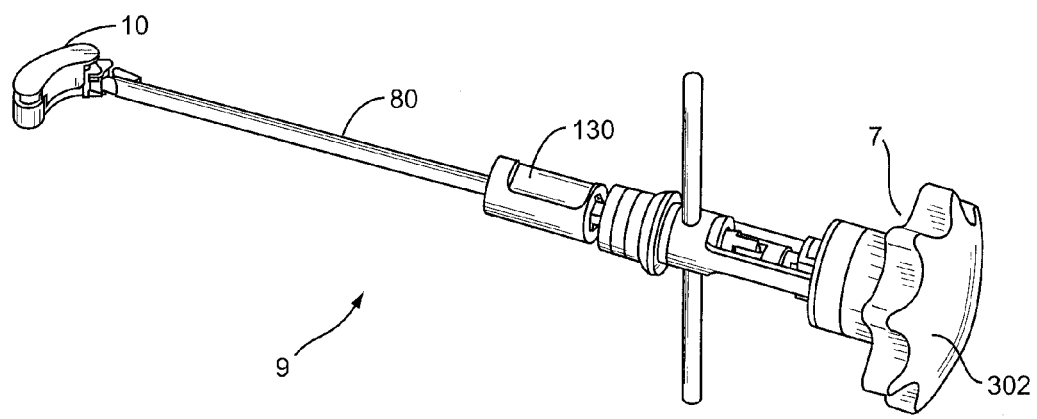
FIG. 16 is a perspective view of the present invention according to one embodiment of the present invention.
Figure 17:
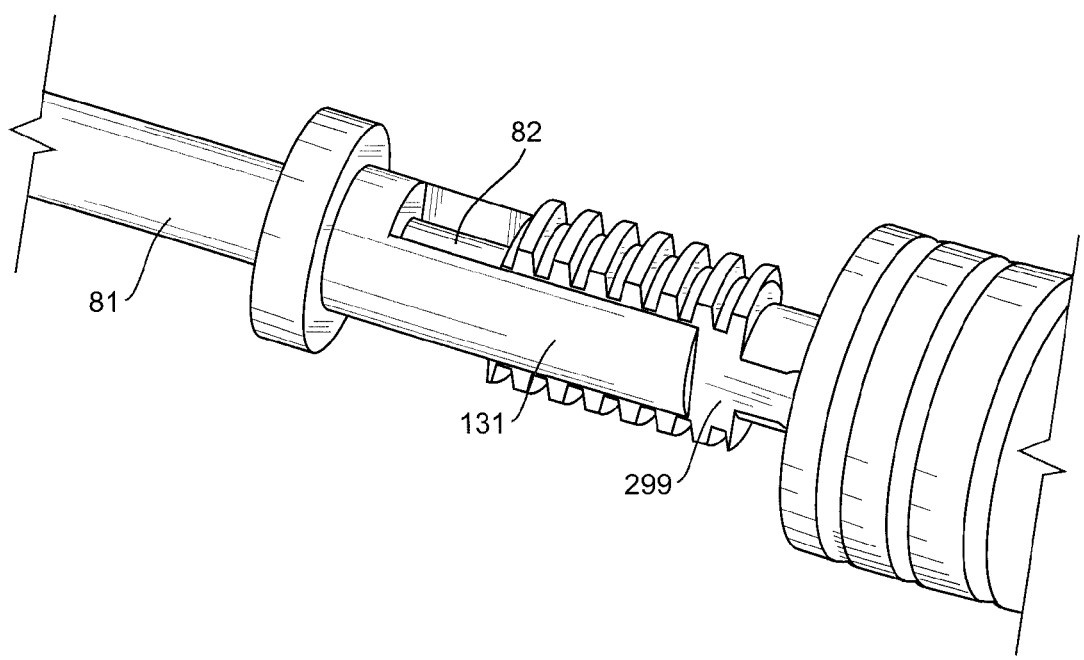
FIG. 17 is a partial perspective view of a section of the device according to one embodiment of the present invention.

The spacer 10 may be articulated relative to the delivery device 80 in a variety of different methods. In one embodiment illustrated in FIGS. 16 and 17, a member 299 is axially aligned with a proximal end of the shaft 82. In one embodiment, member 299 includes a threaded section and a non-threaded section. Proximal end of the shaft 81 includes extensions 131 positioned against the non-threaded section. The shaft 81 moves axially relative to the member 299. A drive sleeve 130 is connected to the shaft 81 and is positioned over the member 299. Drive sleeve 130 includes internally-positioned threads that mate with the threaded section of member 299. Rotation of the drive sleeve 130 causes axial movement of the shaft 81 relative to the shaft 82 thus pivoting the spacer 10. In one embodiment, drive sleeve 130 is attached to the first shaft 81 by a slip ring.

Once properly articulated and positioned between the vertebral members, spacer 10 is deployed from the closed orientation towards the open orientation. A deploying means is positioned within the delivery device 80 to deploy the spacer 10. In one embodiment, a cam 84 is positioned within delivery device and includes a distal end adjacent to the end of the delivery device 80, and a proximal end positioned at the deployer 7. In one embodiment, cam 84 is positioned within the second shaft 82 and is axially moved through the delivery device 80.

Figure 18:
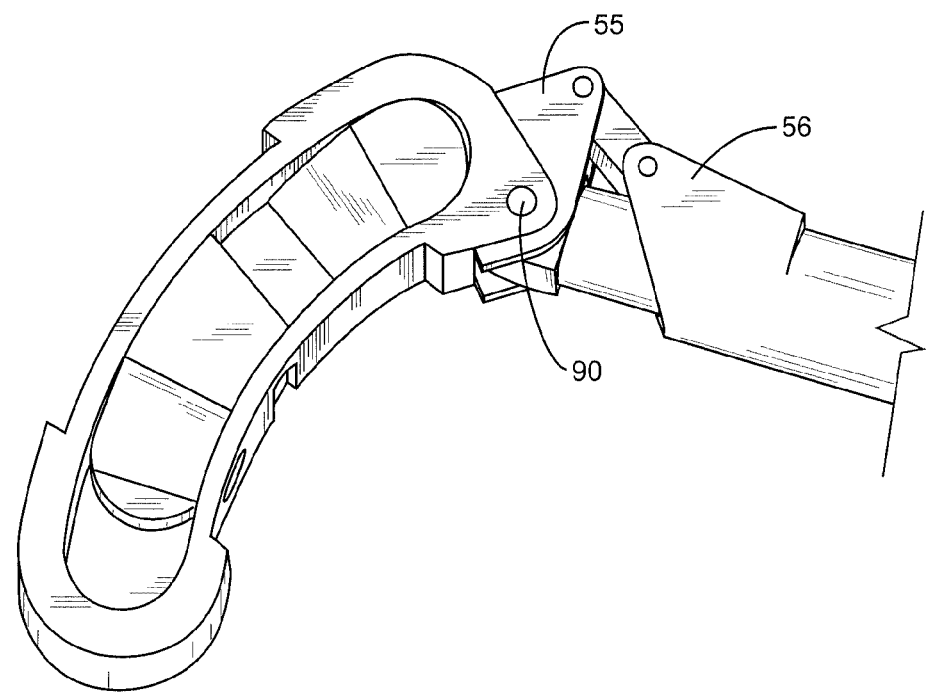
FIG. 18 is a partial perspective view illustrating the third member in a first position within the second member according to one embodiment of the present invention.
Figure 19:
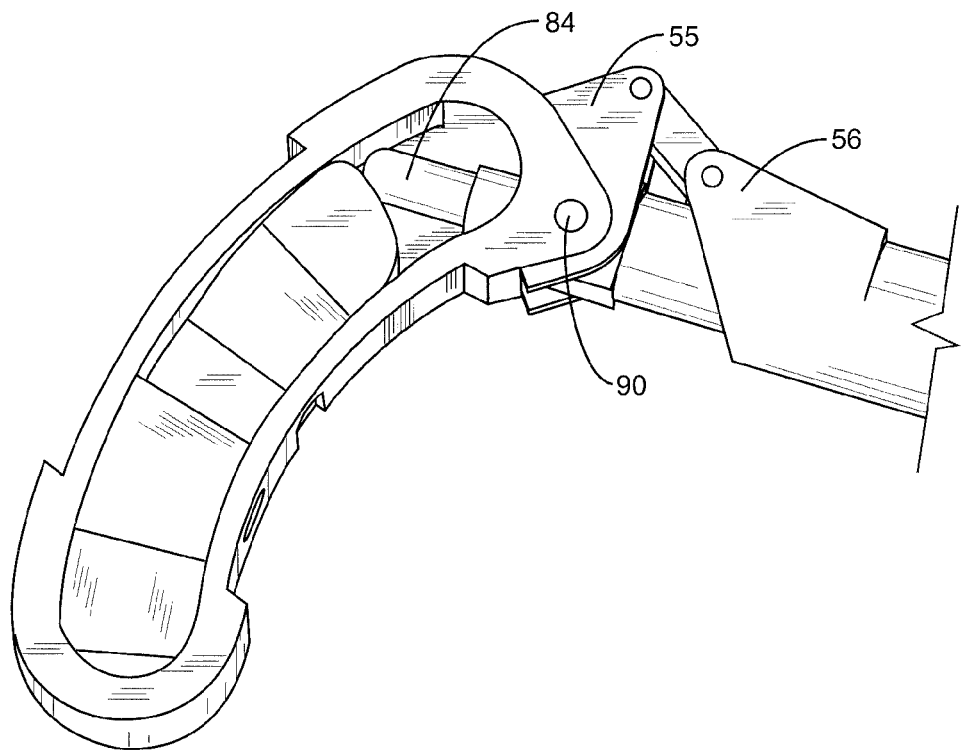
FIG. 19 is a partial perspective view illustrating the third member in a second position within the second member according to one embodiment of the present invention.

Movement of the cam 84 is illustrated in FIGS. 18 and 19. In the closed orientation, delivery device 80 is attached to the spacer 10 with the cam 84 in a first position and third member 40 positioned at the proximal end of the spacer 10. Cam 84 is axially moved within the delivery device 80 to move the third member 40 towards the distal end of the spacer 10. A distal end of the cam 84 contacts a proximal end of the third member 40 to push the third member 40 and deploy the spacer 10. The amount of axial movement of the cam 84 controls the amount of spacer deployment. Axial movement of the cam 84 from the first orientation to the second orientation causes the third member 40 to move relative to the first member 20 causing the angled sections to contact and increase the spacer height. The amount of movement of the cam 84 controls the amount of increase of spacer height. The cam 84 is operatively connected to the third member 40 meaning it may be attached to the third member 40, or unattached but placed in contact with the third member 40 during actuation.

Figure 22:
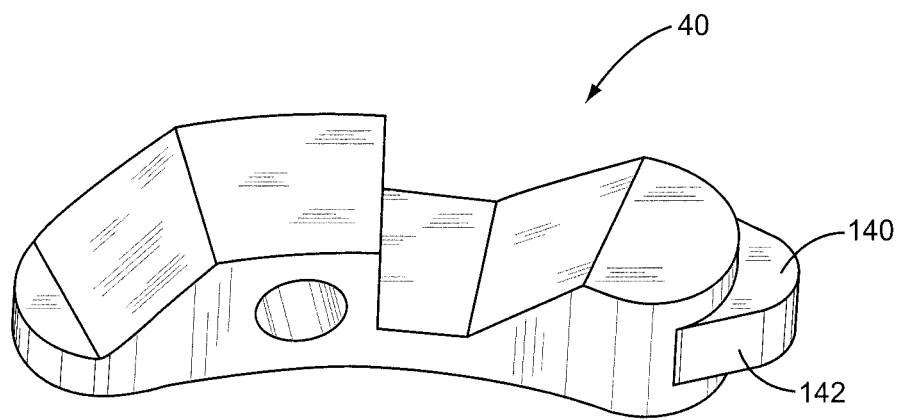
FIG. 22 is a perspective view of another embodiment of the third member constructed according to one embodiment of the present invention.
Figure 23:
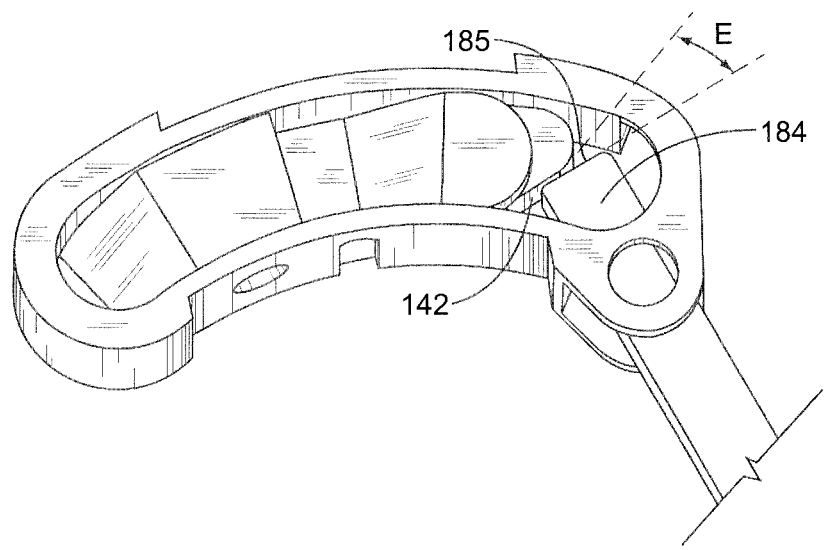
FIG. 23 is a partial perspective view of the cam in contact with the third member constructed according to one embodiment of the present invention.

FIG. 22 illustrates another embodiment of the third member 40. This embodiment is similar to the previous embodiment illustrated in FIG. 4, with the addition of a lug 140 on a proximal end. Lug 140 includes a contact surface 142 that is contacted to the distal end of the cam 84 during the deployment. FIG. 23 illustrates another embodiment of the cam 184 having a distal end 185 that contacts the contact surface 142. In one embodiment, the distal end 185 is substantially perpendicular with the side edges. The contact surface 142 and distal end 185 are shaped such that a contact angle E formed between the two surfaces is maintain as small as possible during the deployment. Additionally, there is a greater amount of contact between the distal end 185 and contact surface 142 during deployment. Cam 184 may have a variety of configurations, including a pushrod that extends along all or a section of the delivery device 80 and includes a distal end 185 that contacts the spacer to deploy it to the expanded size.

In an embodiment having only first and second members (i.e., no third member), the first member has angled surfaces that contact a second member having angled surfaces. Cam 84 is positioned to contact one of the first or second members and provide relative movement for deployment.

FIGS. 6 and 7 illustrate the movement of the third member 40 caused by the cam 84. In one embodiment, third member 40 is positioned proximally within the spacer 10 as illustrated in FIG. 6. Movement of the cam 84 moves the third member 40 distally as illustrated in FIG. 7 causing the spacer 10 to deploy. One manner of reducing the spacer 10 is by moving the cam 84 proximally and pulling the third member 40.

FIG. 1 illustrates one embodiment of the delivery device 80 and deployer 7. Various types of deployers can be applied to the delivery device 80 to expand the spacer 10. The deployer may be positioned adjacent to the spacer 10, or positioned distant from the spacer 10 to be outside the patient. Previously filed U.S. patent application Ser. No. 10/178,960 entitled Minimally Invasive Expanding Spacer and Method, filed Jun. 25, 2002 and assigned to the same entity as the present application, now U.S. Pat. No. 7,087,055, discloses deployers and structures for deploying the spacer towards the open orientation and is herein incorporated by reference in its entirety.

In one embodiment, deployer 7 is attached to a proximal end of the delivery device 80. Deployer 7 is attached to a lock 89 that is attached to the cam 84. Deployer 7 provides axially movement of the cam 84 through the delivery device 80. In one embodiment, knob 302 includes a threaded connection to a contact member. Rotation of the knob causes the contact member to move outward relative to the knob 302. When the deployer 7 is mounted to the delivery device 80, contact member abuts against the proximal end of the lock 89. Rotation of the knob 302 causes the contact member to axially move the lock 89 and thus the cam 84.

Figure 20:
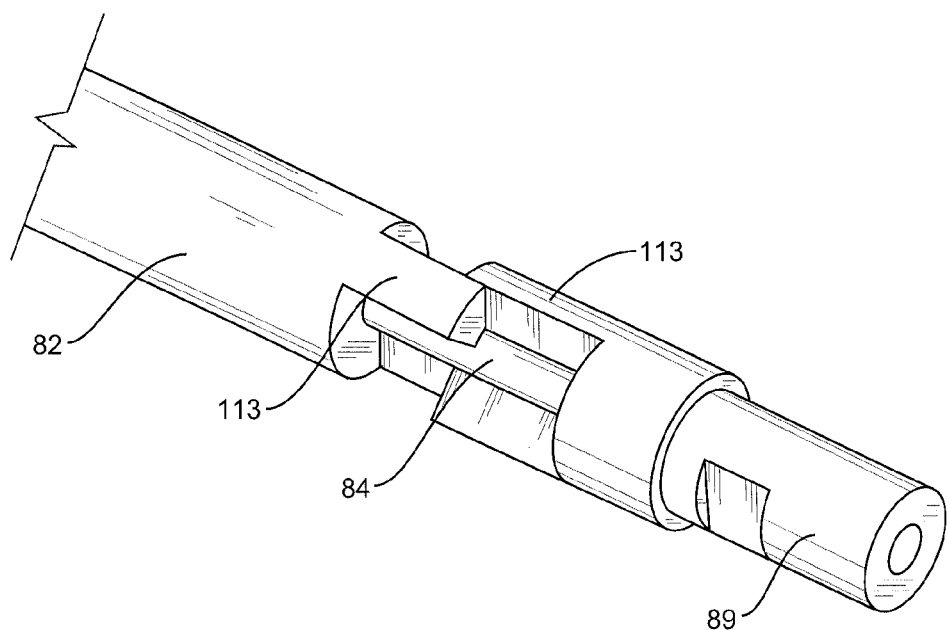
FIG. 20 is a partial perspective view of a lock according to one embodiment of the present invention.

In one embodiment, the amount of axial movement of the cam 84 is controlled. FIG. 20 illustrates one embodiment with the lock 89 positioned an axial distance from the shaft 82 (i.e., FIG. 20 illustrates the cam 84 in a retracted position). Movement of the deployer 7 causes the lock 89 and cam 84 to move axially relative to the shaft 82. The amount of movement is limited as the distal end of the lock 89 contacts the proximal edge of the shaft 82. Various other types of deploying mechanisms may be used for axially moving the cam 84 and deploying the spacer 10.

Figure 21:
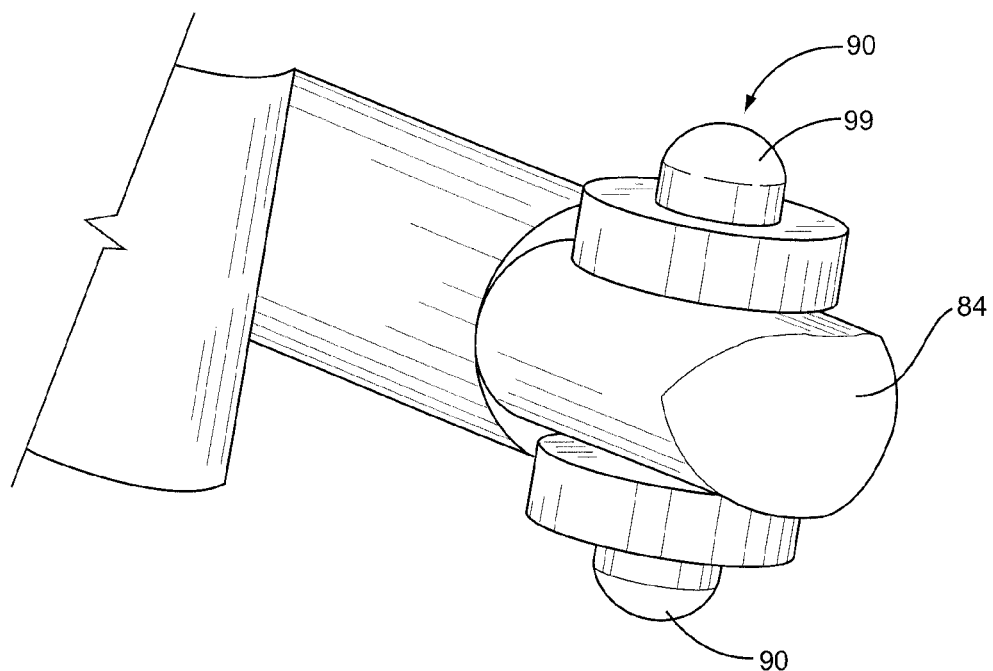
FIG. 21 is a partial perspective view of live pivots according to one embodiment of the present invention.

Delivery device 80 may be attached to the spacer 10 in a variety of different manners. In one embodiment, spacer 10 is connected through movable live pivots 90 that extend through apertures 37. The live pivots 90 connect the spacer 10 to the delivery device 80. In a detached orientation, live pivots 90 are moved below the apertures 57 and the delivery device 80 is detached from the spacer 10. One embodiment is illustrated with FIG. 21. Cam 84 extends through the delivery device 80 and has an extended configuration with a first dimension larger than a second dimension. Pivots 90 are positioned adjacent to the cam 84. In the attached orientation, cam 90 is orientated with the larger dimension aligned relative to the pivots 90. The pivots 90 contact the cam 84 and extend outward through the apertures 57. In the detached orientation, cam 84 is rotated such that the smaller dimension contacts the pivots 90. The pivots 90 retract and the top edge 99 moving away from the apertures 37. In one embodiment, cam 84 is structured with the larger and smaller dimensions being separated by about 90° (i.e., rotation of the cam 84 about 90° results in movement between the attached and detached orientation). In one embodiment, pivots 90 include a rounded surface 91 to facilitate detachment of the spacer 10. In one embodiment, cam 84 is retracted prior to the spacer 10 being detached from the delivery device 80. Embodiments of an attachment, delivery, and deployment device and method are disclosed in U.S. patent application Ser. No. 10/202,918, now U.S. Pat. No. 7,572,276, entitled Minimally Invasive Instruments and Methods for Inserting Implants, filed on Jul. 25, 2002 and assigned to the same entity as the present application, herein incorporated by reference in its entirety.

In one embodiment, cam 84 extends through a section of the delivery device 80 and is accessed towards a proximal end of the delivery device 80. A physician using the apparatus 9 rotates the cam 84 from a point exterior to the patient for detaching the spacer 10 from the delivery device 80. One embodiment is illustrated in FIG. 20 with cam 84 extending through the shaft 82 and being attached to the lock 89. The lock 89 is fixedly attached to the cam 84 with rotation of the lock 89 causing rotation of the cam 84. A proximal end of the shaft 82 and a distal end of the lock 89 have corresponding fingers 113 that control the amount of cam rotation. Rotation of the lock 89 relative to the shaft 82 is limited to a predetermined range because the fingers 113 will contact and prevent further rotation. In one embodiment, fingers 113 are positioned to limit rotation to about 90°. Previously filed U.S. patent application Ser. No. 10/178,960, which has already been incorporated by reference in its entirety, discloses several different types of delivery devices and structures for controlling the spacer.

Figure 24:
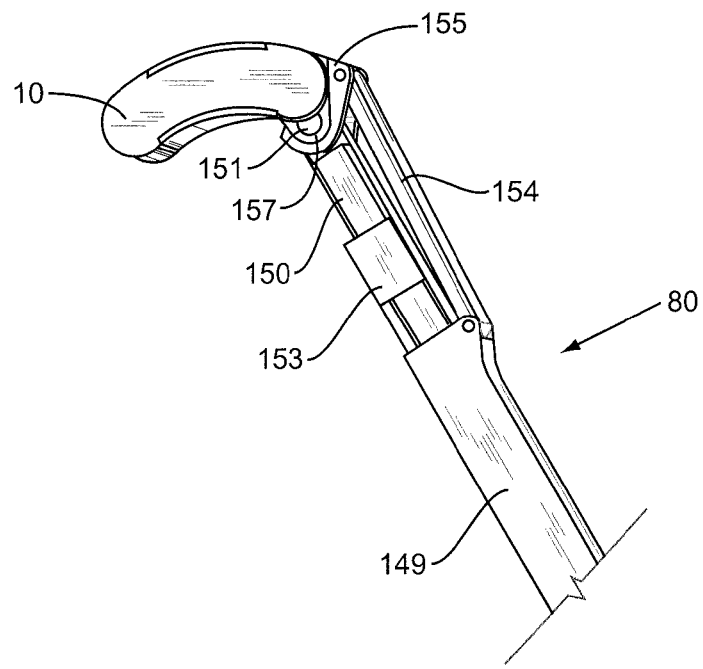
FIG. 24 is a partial perspective view of another delivery device and release mechanism constructed according to one embodiment of the present invention.
Figure 25:
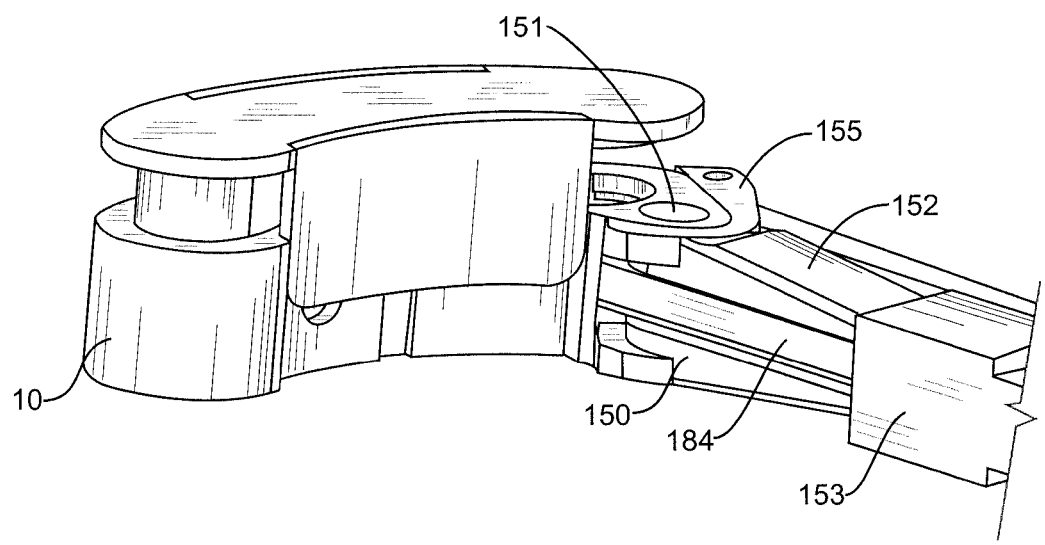
FIG. 25 is a partial perspective view of the spacer attached to the delivery device constructed according to one embodiment of the present invention.

FIGS. 24 and 25 illustrate another embodiment of the detachment device to disconnect the spacer 10 from the delivery device 80. The delivery device 80 includes a drive sleeve 149 with a tube sleeve 150 at a distal end. A release sleeve 153 having a predetermined width is slidably positioned over the tube sleeve 150. A pushrod 184 extends within the tube sleeve 150 and includes a distal end 185 that deploys the spacer 10. Extensions 151 are positioned towards the distal end of the tube sleeve 150 and mount within apertures 157 of a holder 155 and apertures 37 within the spacer 10. The spacer 10 pivots about the extensions 151 as it is connected to the delivery device 80. A link 154 extends between the holder 155 and drive sleeve 149. Relative movement of the drive sleeve 149 relative to the tube sleeve 150 causes the spacer to pivot.

Figure 26:
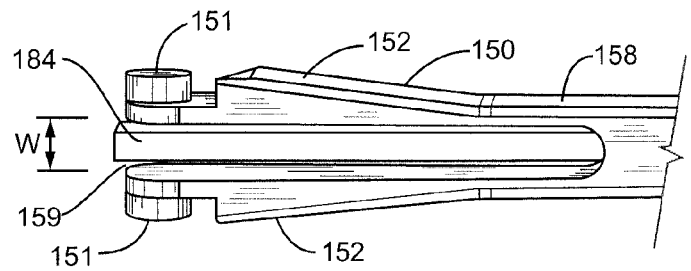
FIG. 26 is a partial perspective view of the tube sleeve and cam constructed according to one embodiment of the present invention.

As illustrated in FIG. 26, tube sleeve 150 includes a distal end having one or two ramped surfaces 152. The ramped surfaces 152 gradually increase along the tube sleeve 150 to a maximum height at a point adjacent to the extensions 151. A slot 159 is formed on the distal end of the tube sleeve 150 between the ramped surfaces 152. The slot 159 has a width w when the extensions 151 are mounted to the spacer 10.

The release sleeve 153 is slidably mounted on the tube sleeve 150. The release sleeve 153 has a predetermined width that is greater than the width of a first section 158 of the tube sleeve 150 away from the ramped surfaces 152, but less than a width of the ramped surfaces 152.

Figure 27:
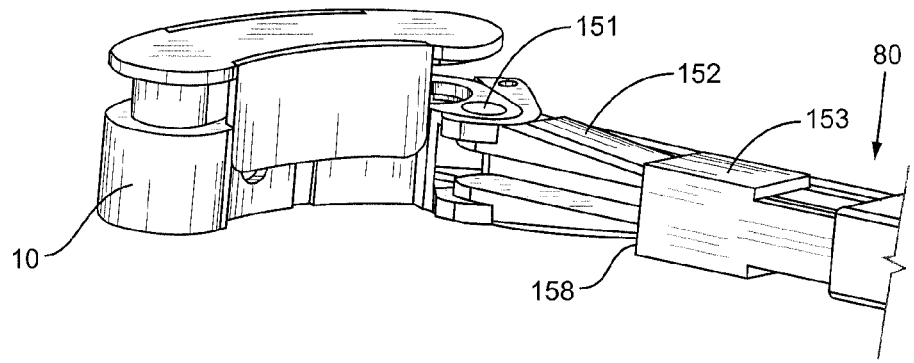
FIG. 27 is a partial perspective view of the spacer attached to the delivery device constructed according to one embodiment of the present invention.
Figure 28:
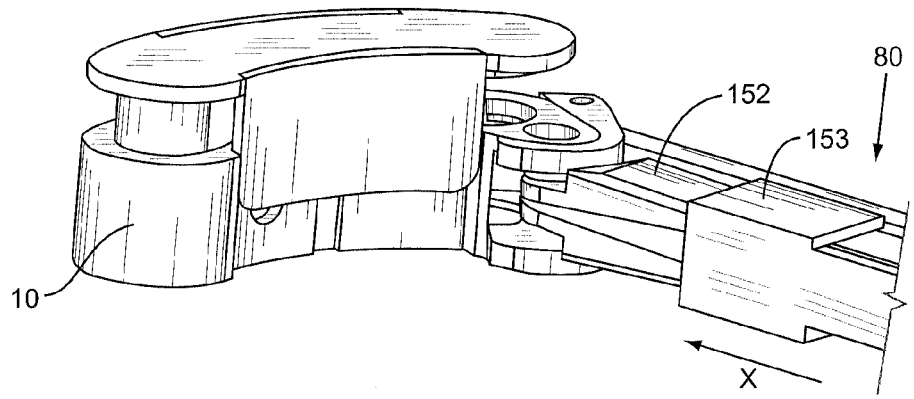
FIG. 28 is a partial perspective view of the spacer detached from the delivery device constructed according to one embodiment of the present invention.

FIGS. 27 and 28 illustrate the disconnecting of the delivery device 80 from the spacer 10. In FIG. 27, the spacer 10 is connected to the delivery device 80 as the extensions 151 are positioned through the holder 155 and spacer 10. The release sleeve 153 is positioned away from the extensions on a first section 158 of the tube sleeve 152. FIG. 28 illustrates the spacer 10 being disconnected from the delivery device 80. Release sleeve 153 has been distally moved in the direction of arrow x along the ramped surfaces 152 of the tube sleeve 150. This causes the ramped surfaces 152 to be forced inward thus reducing the width w. Extensions 151 mounted to the distal end of the tube sleeve 150 likewise are forced inward and detach from the spacer 10. At this point, the spacer 10 can be removed from the delivery device 80. The holder 155 remains attached to the delivery device 80 and is removed leaving only the spacer 10 within the patient.

In one embodiment, the pushrod 184 extends through the slot 159 in the tube sleeve 150 and prevents the spacer 10 from being disconnected. While the pushrod 184 is within the slot 159, the ramped surfaces 152 are prevented from being forced together and therefore the extensions 151 remain within the spacer 10. Once the pushrod 184 is removed (i.e., moved in a "−" direction), the ramped surfaces 152 can be forced together with the width w reduced to remove the extensions 151 from the spacer 10. In another embodiment, there is adequate clearance between the pushrod 184 and the ramped surfaces to allow the width w of the opening 159 to be reduced and the spacer detached. In one embodiment, an attachment may extend from the release sleeve 153 towards the proximal end of the delivery device 80 to allow a physician to release the spacer 10 from a remote position.

In another embodiment, delivery device 80 may be attached to the spacer 10 via a shearable pin that is designed to fail once the spacer 10 is deployed. Once the pin is sheared, the delivery device 80 is removed from the spacer 10. In another embodiment, delivery device 80 is attached to the spacer 10 by threads. Rotation of the delivery device 80 relative to the spacer 10 causes the spacer to dislocate from the device 80. In another embodiment, delivery device 80 and spacer 10 are equipped with a half turn locking system such that rotation of the delivery device 80 relative to the spacer 10 causes dislocation.

The delivery device 80 may remain attached to the spacer 10 or may be detached from the spacer during use. Removing the delivery device 80 may be necessary to provide additional operating space for the physician during the procedure as the delivery device 80 may interfere with other equipment, or the vision if it were left attached to the spacer 10. In this usage, the delivery device 80 may further be reattached to the spacer 10 for removal from the patient at the end of the procedure. In another usage, the delivery device 80 is removed and the spacer 10 remains permanently within the patient.

In one embodiment, cam 84 extends through the shaft 82 and includes a proximal end mounted to the lock mechanism 89. In one embodiment, cam 84 is not connected to a lock. In one embodiment, cam 84 is axially movable and rotatable within the shaft 82. In one embodiment, the second shaft 82 is mounted within the first shaft 81. In one embodiment, the first shaft 81 is sized to slide along the exterior of the second shaft 82. In one embodiment, the second shaft 82 is axially stationary during the articulating and deploying processes. In one embodiment, member 200 is stationary during the articulating process.

The term vertebral member is used generally to describe the vertebral geometry comprising the vertebral body, pedicles, lamina, and processes. The spacer 10 may be sized and shaped, and have adequate strength requirements to be used within the different regions of the vertebra including the cervical, thoracic, and lumbar regions. In one embodiment, spacer 10 has a load capacity of about 2000 lbf.

The spacer may be positioned within the disc space between adjacent vertebras. Contact surfaces 21, 31 contact the end plates of the vertebra to space the vertebra as necessary. The spacer 10 may be inserted posteriorly, anteriorily, or laterally into the patient.

The contact surfaces 21, 31 may be porous to allow bone ingrowth into the spacer 10. One or both contact surfaces 21, 31 may include one or more apertures. Bone growth material is positioned within the apertures to accommodate bone growth through the entire implant. The bone growth material may include a sponge, matrix, and/or other carrier impregnated with a protein such as bone morphogenic protein (BMP), LIM mineralization protein (LMP), etc.

In one embodiment, the spacer 10 is deployed using a pair of levers. In one embodiment, the spacer is deployed with an instrument having a pair of offset arms similar to a scissors.

The present invention may be carried out in other specific ways than those herein set forth without departing from the scope and essential characteristics of the invention. In one embodiment, spacer 10 and delivery device 80 are constructed of stainless steel. In one embodiment, support sections are positioned distally of the angled surfaces. In one embodiment, the cam 184, 84 is a pushrod. In one embodiment the biasing member 108 is a coil spring. In one embodiment, when the spacer 10 is in the open orientation the angled surfaces of the members are in contact. In one embodiment, second member 30 does not include sidewalls 33, and the third member 40 has a width smaller than or equal to the width of the second member 30. In one embodiment, spacer 10 is constructed of titanium. In one embodiment, the apertures 37 in the spacer are about 3.5 mm in diameter. The present embodiments are, therefore, to be considered in all respects as illustrative and not restrictive, and all changes coming within the meaning and equivalency range of the appended claims are intended to be embraced therein.

What is claimed is:

1. A device to space vertebral members comprising:
a first member having an interior side with a first angled section and an exterior side with a first contact surface;
a second member having a second interior side and a second exterior contact surface;
a third member positioned between the first member and the second member, the third member having a first side with a second angled section positioned towards the first angled section, and a second side positioned towards the interior surface of the second member;
the device positionable between a first orientation with the first angled section engaged with the second angled section and having a first maximum height extending between the first contact surface and the second exterior contact surface and a second orientation with the first angled section spaced apart from the second angled section and having an increased second maximum height between the first contact surface and the second exterior contact surface.

2. The device of claim 1, wherein the second interior side of the second member and the second side of the third member are both substantially flat.

3. The device of claim 1, wherein the first contact surface and the second exterior contact surface are substantially parallel when the device is in the first orientation.

4. The device of claim 1, wherein the first contact surface and the second exterior contact surface form an acute angle when the device is in the second orientation.

5. The device of claim 1, wherein:
the first member comprises a third angled section and the third member comprises a fourth angled section; and
the third angled section engages the fourth angled section when the device is in the first orientation and is spaced apart from the fourth angled section when the device is in the second orientation.

6. The device of claim 5, wherein the first angled section and the third angled section are spaced apart by a planar surface that extends parallel to the first contact surface.

7. The device of claim 5, wherein the first angled section extends at a first angle relative to the first contact surface and the third angled surface extends at a second angle relative to the first contact surface, the first angle being equal to the second angle.

8. The device of claim 5, wherein the first angled section extends at a first angle relative to the first contact surface and the third angled surface extends at a second angle relative to the first contact surface, the first angle being different than the second angle.

9. The device of claim 8, wherein there is a difference between about 20 degrees and about 40 degrees between the first and second angles.

10. The device of claim 5, wherein the second angled section extends at a first angle relative to the second side and the fourth angled surface extends at a second angle relative to the second, the first angle being different than the second angle.

11. The device of claim 10, wherein there is a difference between about 20 degrees and about 40 degrees between the first and second angles.

12. The device of claim 1, further comprising a shaft movably positioned through a sidewall of the second member so as to engage the third member to move the third member relative to the first member to move the device from the first orientation to the second orientation.

13. The device of claim 12, wherein a proximal end of the third member engages an inner surface of the sidewall when the device is in the first orientation and is spaced apart from the inner surface when the device is in the second orientation.

14. The device of claim 12, wherein a distal end of the third member engages an inner surface of the sidewall when the device is in the second orientation and is spaced apart from the inner surface of the sidewall when the device is in the first orientation.

15. The device of claim 1, wherein at least one of the first contact surface and the second exterior contact surface comprises ridges configured to stabilize the device when the first contact surface and the second exterior contact surface engage vertebral members.

16. The device of claim 1, wherein the third member comprises a first aperture extending through a first lateral wall of the third member and a second aperture extending through an opposite second wall of the third member.

17. The device of claim 16, wherein the first aperture is coaxial with the second aperture.

18. The device of claim 1, wherein the second member second interior side and the third member second side are both substantially flat such that the second side slides along the second interior side as the device moves between the first and second orientations.

19. A method to space apart vertebral members, comprising:
- positioning the device of claim 1 between the vertebral members with the device in the first orientation; and
- moving the device from the first orientation to the second orientation.

20. The method of 19, wherein the first contact surface and the second exterior contact surface are substantially parallel when the device is in the first orientation and the first contact surface and the second exterior contact surface form an acute angle when the device is in the second orientation.

* * * * *